(12) United States Patent
Miyamoto

(10) Patent No.: US 9,427,199 B2
(45) Date of Patent: Aug. 30, 2016

(54) MEDICAL IMAGE DISPLAY CONTROL APPARATUS, MEDICAL IMAGE DISPLAY CONTROL METHOD, AND MEDICAL IMAGE DISPLAY CONTROL PROGRAM

(71) Applicant: FUJIFILM Corporation, Tokyo (JP)

(72) Inventor: Masaki Miyamoto, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 14/486,754

(22) Filed: Sep. 15, 2014

(65) Prior Publication Data

US 2015/0035829 A1 Feb. 5, 2015

Related U.S. Application Data

(63) Continuation of application No. PCT/JP2013/001644, filed on Mar. 13, 2013.

(30) Foreign Application Priority Data

Mar. 21, 2012 (JP) ................................ 2012-063588

(51) Int. Cl.
*G06T 15/30* (2011.01)
*A61B 6/00* (2006.01)
(Continued)

(52) U.S. Cl.
CPC ............. *A61B 6/466* (2013.01); *A61B 5/055* (2013.01); *A61B 5/742* (2013.01); *A61B 6/032* (2013.01); *A61B 6/503* (2013.01); *A61B 6/504* (2013.01); *A61B 6/5223* (2013.01); *G06T 15/005* (2013.01); *G06T 17/10* (2013.01);

(Continued)

(58) Field of Classification Search
None
See application file for complete search history.

(56) References Cited

U.S. PATENT DOCUMENTS

| 6,248,070 B1 | 6/2001 | Kanda et al. |
| 2010/0074487 A1 | 3/2010 | Miyamoto et al. |
| 2010/0201687 A1 | 8/2010 | Breeuwer et al. |

FOREIGN PATENT DOCUMENTS

| JP | S63-214232 A | 9/1988 |
| JP | 2000-139917 A | 5/2000 |

(Continued)

OTHER PUBLICATIONS

International Search Report (ISR) (PCT Form PCT/ISA/210), in PCT/JP2013/001644, dated Jun. 11, 2013.

(Continued)

*Primary Examiner* — Peter Hoang
(74) *Attorney, Agent, or Firm* — McGinn IP Law Group PLLC

(57) ABSTRACT

A functional image generating section that generates a functional image that represents the functions of a subject, based on 3D medical image data obtained by imaging the subject; a projected 3D image generating section that generates a projected 3D image that represents the appearance of the subject, based on the 3D medical image data; a display control section that displays the functional image and the projected 3D image; and a specified position data obtaining section that obtains position data regarding a position specified within the functional image, are provided. The projected 3D image generating section generates the projected 3D image which is projected in a projection direction such that a position within the projected 3D image corresponding to the specified position faces forward, based on the position data. The display control section displays the projected 3D image having the projection direction.

15 Claims, 8 Drawing Sheets

(51) Int. Cl.
  *A61B 5/055* (2006.01)
  *A61B 5/00* (2006.01)
  *G06T 15/00* (2011.01)
  *G06T 17/10* (2006.01)
  *G06T 17/20* (2006.01)
  *G06T 19/20* (2011.01)
  *A61B 6/03* (2006.01)

(52) U.S. Cl.
  CPC .............. *G06T 17/20* (2013.01); *G06T 19/20* (2013.01); *A61B 6/469* (2013.01); *G06T 2210/41* (2013.01); *G06T 2219/2004* (2013.01)

(56) References Cited

FOREIGN PATENT DOCUMENTS

| | | |
|---|---|---|
| JP | 2004-181041 A | 7/2004 |
| JP | 2008-173236 A | 7/2008 |
| JP | 2008-253753 A | 10/2008 |
| JP | 2009-18005 A | 1/2009 |
| JP | 2010-246777 A | 11/2010 |
| JP | 2010-537701 A | 12/2010 |
| JP | 2011-206297 A | 10/2011 |
| WO | WO 2009/031081 A2 | 3/2009 |

OTHER PUBLICATIONS

Japanese Office Action dated May 19, 2015 with an English translation thereof.

Japanese Office Action dated Mar. 1, 2016 with an English translation.

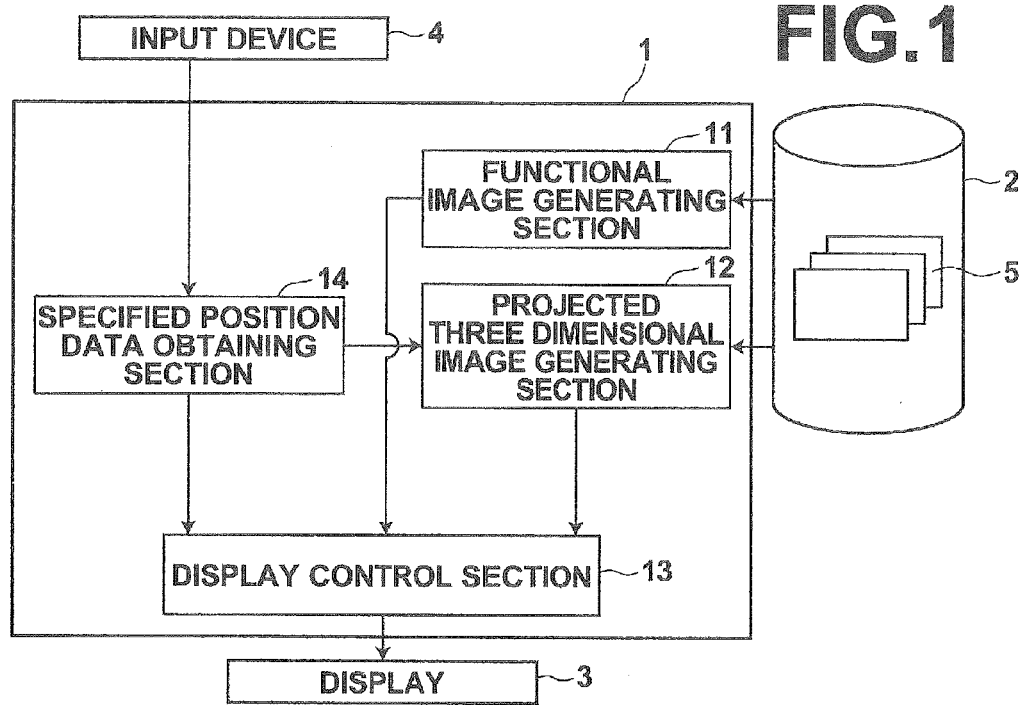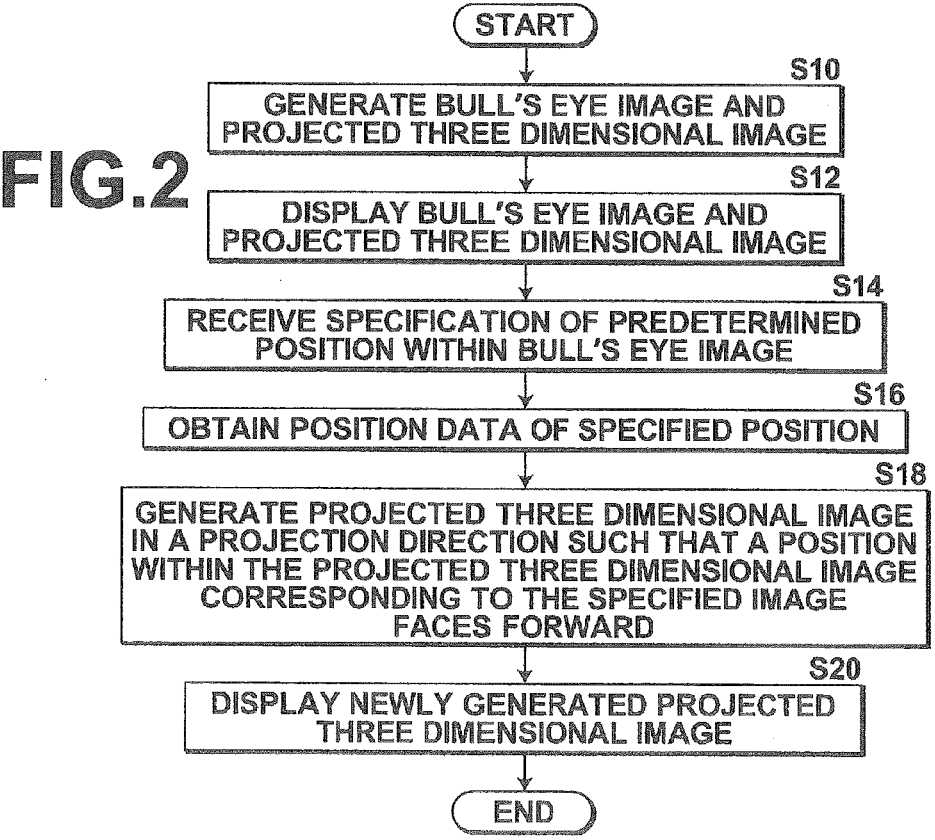

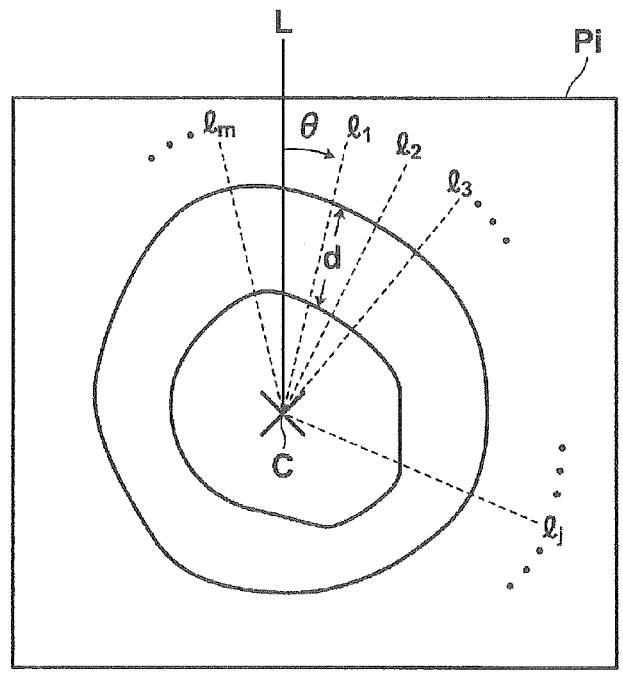
FIG.4
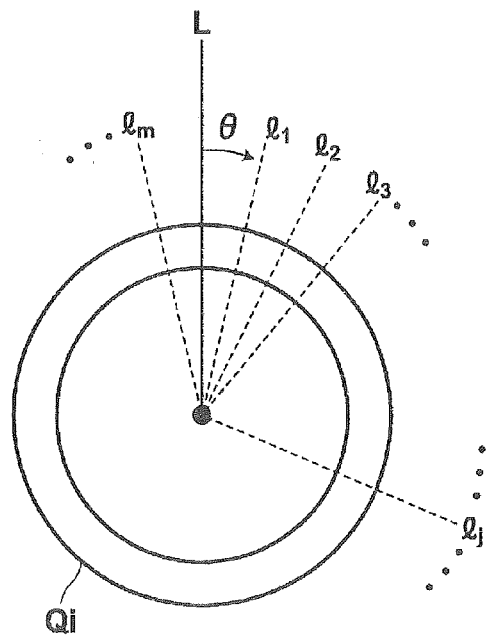

MEDICAL IMAGE DISPLAY CONTROL APPARATUS, MEDICAL IMAGE DISPLAY CONTROL METHOD, AND MEDICAL IMAGE DISPLAY CONTROL PROGRAM

CROSS REFERENCE TO RELATED APPLICATIONS

This application is a Continuation of PCT International Application No. PCT/JP2013/001644 filed on Mar. 13, 2013, which claims priority under 35 U.S.C. §119(a) to Japanese Patent Application No. 2012-063588 filed on Mar. 21, 2012. Each of the above applications is hereby expressly incorporated by reference, in its entirety, into the present application.

BACKGROUND OD THE INVENTION

1. Technical Field

The present invention is related to a medical image display control apparatus, a medical image display control method, and a medical image display control program, that display both a functional image and a projected three dimensional image of a subject.

2. Background Art

Conventionally, the Bull's Eye display method is employed as a display method that indicates the functions of the heart (refer to Japanese Unexamined Patent Publication No. 2008-253753, for example). The bull's eye display method is a method that concentrically arranges and displays images that represent evaluations of the functions of a heart as planes sliced at constant intervals in a direction that traverses the major axis of an ellipse, when the heart is considered as an approximate ellipsoidal model. In the bull's eye display method, the functions of the sliced planes near one of the apexes of the major axis of the ellipsoidal model are placed close to the center of the concentric circles, and the functions of the sliced planes near the other of the apexes of the major axis of the ellipsoidal model are placed toward the exterior of the concentric circles.

This display method is used mainly with functional images as the targets of display. Functional images include those taken directly by myocardial scintigraphy (SPECT), and functional images obtained from the results of analyzing images taken by CT (Computed Tomography)/MRI (Magnetic Resonance Imaging).

Here, functional images displayed by the bull's eye display method represent evaluations of the functions of the heart, and do not accurately represent the morphology of the heart. Therefore, it is only possible to roughly understand what positions of the heart correspond to positions within the functional images.

Meanwhile, it has become possible to observe coronary arteries within projected three dimensional images which are reconstructed using three dimensional medical image data imaged by CT and the like. Not only is it possible to understand positions of the heart within projected three dimensional images, but it is also possible to observe blood vessels that influence functions of the heart in the case that functional deterioration of the heart occurs. However, because projected three dimensional images are images that represent the three dimensional form of subjects such as a heart, what part of the heart or the like is causing the functional deterioration cannot be understood merely by observing the projected three dimensional images.

Therefore, correlating and displaying the aforementioned functional images and projected three dimensional images has been considered. For example, Japanese Unexamined Patent Publication No. 2004-181041 discloses displaying projected three dimensional images, in which regions specified within functional images are colored differently.

In addition, Japanese Unexamined Patent Publication No. 2000-439917 discloses a method in which three dimensional morphological images and functional images are combined and displayed.

DISCLOSURE OF THE INVENTION

However, even if a region specified within a functional image is displayed in a different color within a projected three dimensional image as in the method disclosed in Japanese Unexamined Patent Publication No. 2004-181041, the morphology of the blood vessel or the like in the colored portion cannot be understood in the case that the colored portion is toward the rear of the projected three dimensional image. That is, even if a position corresponding to a position specified within a functional image is displayed within a projected three dimensional image, there are cases in which the corresponding position is at the edge (the position indicated by the marker in FIG. 16) of the projected three dimensional image as illustrated in FIG. 16, and cases in which the corresponding position is at the rear (the position indicated by the marker in FIG. 17) of the projected three dimensional image as illustrated in FIG. 17. In such cases, the morphology of blood vessels or the like cannot be understood.

In addition, the method disclosed in Japanese Unexamined Patent Publication No. 2000-139917 is also not capable of solving the aforementioned problem.

The present invention has been developed in view of the foregoing circumstances. It is an object of the present invention to provide a medical image display control apparatus, a medical image display control method, and a medical image display control program, that display both functional images and projected three dimensional images of a subject, that enable easy and expedient observation of blood vessels or the like.

A medical image display control apparatus of the present invention comprises:

a functional image generating section that generates a functional image that represents the functions of a subject, based on three dimensional medical image data obtained by imaging the subject;

a projected three dimensional image generating section that generates a projected three dimensional image that represents the appearance of the subject, based on three dimensional medical image data obtained by imaging the subject;

a display control section that displays the functional image and the projected three dimensional image on a display section; and a specified position data obtaining section that obtains data regarding a predetermined position which is specified within the functional image which is being displayed on the display section;

the projected three dimensional image generating section generating the projected three dimensional image which is projected in a projection direction such that a position within the projected three dimensional image corresponding to the specified predetermined position faces forward, based on the data regarding the predetermined specified position, when the predetermined position is specified within the functional image; and the display control section displaying the projected three dimensional image having the projection direction on the display section.

In the medical image display control apparatus of the present invention, the position within the projected three dimensional image may be the same as a position on the subject represented by the data regarding the position obtained by the specified position data obtaining section.

Alternatively, the position within the projected three dimensional image may be a position which is set in advance within a sectioned region of the functional image that includes the position data obtained by the specified position data obtaining means from among a plurality of sectioned regions into which the functional image is divided.

The position which is set in advance within the sectioned region may be the center position of the sectioned region.

The sectioned regions may be regions which are divided into a plurality of concentric regions and then further divided into a plurality of regions in the circumferential direction.

The sectioned regions may be those in which the functional image is divided into 17 regions.

In the case that the subject is a heart, the projected three dimensional image generating section may generate the projected three dimensional image in the projection direction by administering a rotation process with the longitudinal direction of the heart as an axis of rotation.

Alternatively, in the case that the subject is a heart, the projected three dimensional image generating section may generate the projected three dimensional image in the projection direction by administering a rotation process such that a line segment that connects the center of an ellipsoidal shape that approximates the heart and the position within the projected three dimensional image is directed forward.

A medical image display control method of the present invention comprises:

generating a functional image that represents the functions of a subject, based on three dimensional medical image data obtained by imaging the subject;

generating a projected three dimensional image that represents the appearance of the subject, based on three dimensional medical image data obtained by imaging the subject; and displaying the functional image and the projected three dimensional image on a display section;

data being obtained regarding a predetermined position which is specified within the functional image which is being displayed on the display section when the predetermined position is specified within the functional image;

the projected three dimensional image which is projected in a projection direction such that a position within the projected three dimensional image corresponding to the specified predetermined position faces forward being generated, based on the data regarding the predetermined specified position; and the projected three dimensional having the projection direction being displayed on the display section.

A medical image display control program of the present invention is recorded in a non transitory computer readable medium, and causes a computer to function as:

a functional image generating section that generates a functional image that represents the functions of a subject, based on three dimensional medical image data obtained by imaging the subject;

a projected three dimensional image generating section that generates a projected three dimensional image that represents the appearance of the subject, based on three dimensional medical image data obtained by imaging the subject;

a display control section that displays the functional image and the projected three dimensional image on a display section; and a specified position data obtaining section that obtains data regarding a predetermined position which is specified within the functional image which is being displayed on the display section;

the projected three dimensional image generating section generating the projected three dimensional image which is projected in a projection direction such that a position within the projected three dimensional image corresponding to the specified predetermined position faces forward, based on the data regarding the predetermined specified position, when the predetermined position is specified within the functional image; and the display control section displaying the projected three dimensional image having the projection direction on the display section.

According to the medical image display control apparatus, the medical image display control method, and the medical image display control program of the present invention, both a functional image and a projected three dimensional image are displayed. When a predetermined position is specified within the functional image which is displayed on the display section, a projected three dimensional image which is projected in a projection direction such that the position within the projected three dimensional image corresponding to the specified predetermined position faces forward, based on data regarding the specified predetermined position. The generated projected three dimensional image projected in the projection direction is displayed. Therefore, the morphology of blood vessels or the like which are at the position within the projected three dimensional image corresponding to the position within the functional image can be easily and expediently observed.

In addition, the medical image display control apparatus, the medical image display control method, and the medical image display control program of the present invention may adopt configurations in which the functional image is sectioned into a plurality of regions, a projected three dimensional image which is projected in a projection direction such that a position which is set in advance within a sectioned region of the functional image that includes a specified position faces forward when the position is specified within the functional image, and the generated projected three dimensional image is displayed. In this case, even in cases that the position of a cursor that specifies a position within the functional image fluctuates, display of a projected three dimensional image having the same projection direction can be maintained as long as the position fluctuates within a sectioned region. Therefore, fine changes in the projection direction of the projected three dimensional image can be prevented, and a region (sectioned region) which is desired to be observed within the projected three dimensional image can be displayed constantly facing forward.

BRIEF DESCRIPTION OF THE DRAWINGS

FIG. 1 is a block diagram that illustrates the schematic configuration of a medical image display system that employs a first embodiment of the medical image display control apparatus of the present invention.

FIG. 2 is a flow chart for explaining the operation of the medical image display system that employs the first embodiment of the medical image display control apparatus of the present invention.

FIG. 4 is a diagram for explaining the relationship between a bull's eye display and the thickness of the myocardium.

BEST MODE FOR CARRYING OUT THE INVENTION

Figure 3:
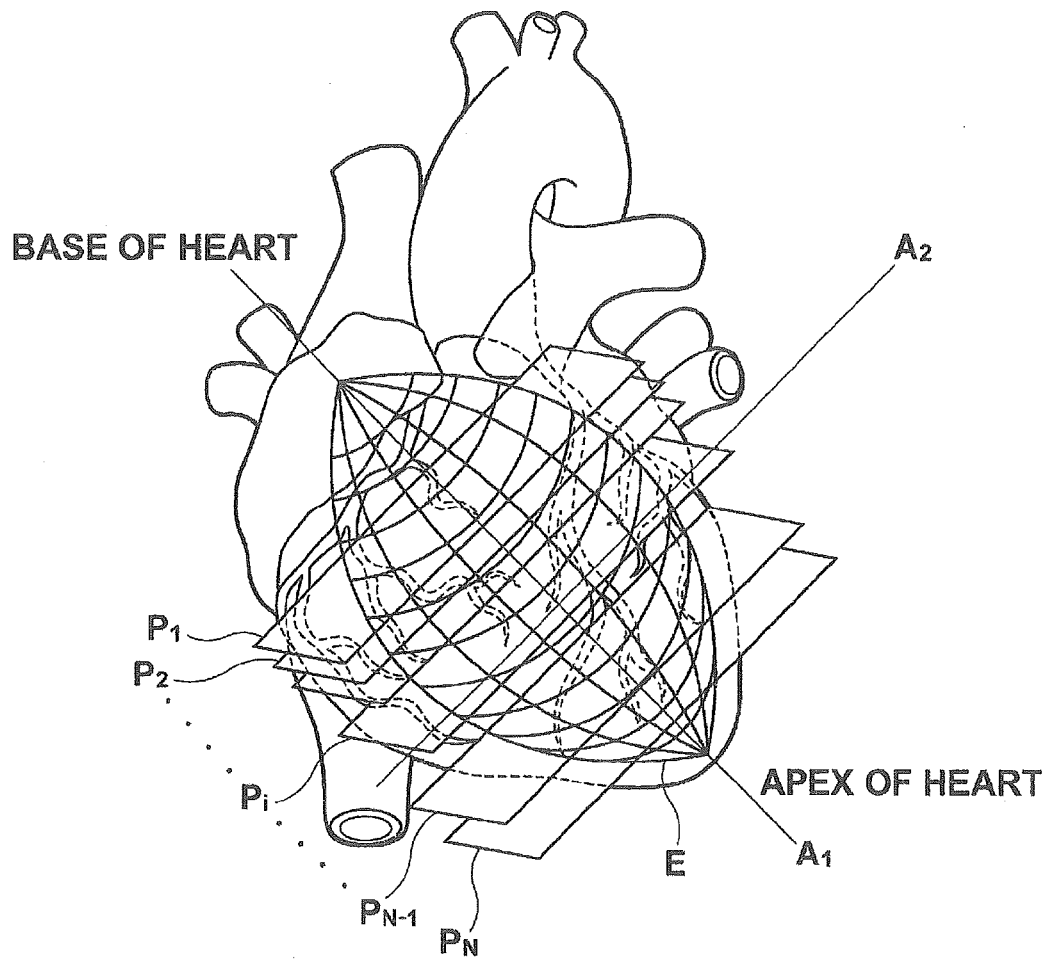
FIG. 3 is a diagram for explaining the relationship between sliced planes and a heart.

Hereinafter, a first embodiment a medical image display control apparatus, a medical image display control method, and a medical image display control program of the present invention will be described in detail with reference to the attached drawings. FIG. 1 is a block diagram that illustrates the schematic configuration of a medical image display system that employs the first embodiment of the medical image display control apparatus of the present invention.

As illustrated in FIG. 1, the medical image display system of the present embodiment is equipped with a medical image display apparatus 1, a storage device 2, a display 3, and an input device 4.

The medical image display apparatus 1 is a single computer, in which the first embodiment of the medical image display control program of the present invention is installed. The computer may be a workstation or a personal computer that a physician who performs diagnostic imaging directly operates. Alternatively, the computer may be a server computer which is connected to the work station or the personal computer via a network. The medical image display program is stored in a recording medium such as a DVD or a CD-ROM, or in a server computer connected to a network to be accessible from the exterior. The medical image display program is read out from the recording medium or the server computer, downloaded into the computer, and installed in response to a request from a physician.

The medical image display apparatus 1 is equipped with a CPU (Central Processing Unit), a semiconductor memory, a storage device such as a hard disk and an SSD (Solid State Drive), in which the medical image display program is installed, etc. These hardware components constitute a functional image generating section 11, a projected three dimensional image generating section 12, a display control section 13, and a specified position data obtaining section 14 as illustrated in FIG. 1. Each of the above sections function by the medical image display control program installed in the hard disk being executed by the central processing unit.

The functional image generating section 11 generates functional images that represent the functions of subjects based on three dimensional medical image data obtained by imaging the subjects with a CT (Computed Tomography) apparatus, an MRI (Magnetic Resonance Imaging) apparatus, etc. Note that in the present embodiment, the subject is a heart.

Functional images are images representing the distribution of evaluation values that represent evaluations of the functions of the heart, according to cardiac movement, the inner diameters of the ventricles of the heart, the thickness of the myocardia, and the like. Specific examples of functional images include images of the inner diameters of ventricles during that represent the diameters of the ventricles during a certain phase, images of the inner diameters of telediastolic ventricles that represent the inner diameters of the ventricles of the heart in a diastolic phase, images of the inner diameters of telesystolic ventricles that represent the inner diameters of the ventricles of the heart in a systolic phase, images of local ejection fractions that represent the ejection fractions of each of a plurality of sectioned regions, images of myocardial wall thicknesses that represent myocardial wall thicknesses at a certain phase, images of telediastolic wall thicknesses that represent myocardial wall thicknesses during the diastolic phase, images of telesystolic wall thicknesses that represent myocardial wall thicknesses during the systolic phase, images of amounts of change in wall thicknesses that represent the difference in myocardial wall thicknesses during the diastolic phase and myocardial wall thicknesses during the systolic phase, images of rates of increase of wall thicknesses that represent values of (B−A)/A when the myocardial wall thickness during the diastolic phase is designated as A and the myocardial wall thickness during the systolic phase is designated as B, and myocardial scintigraphy images.

The functional images that represent myocardial scintigraphy are images that represent data regarding the distribution of an agent that collects in the myocardia, which is injected into a patient's arm, measured from the exterior of the body. The state of blood flow in the myocardia, the metabolism of myocardial tissue, and the functions of nerves can be represented, by changing the agent which is injected.

In the case that evaluations of the movements of the heart are represented in functional images, the functional images are generated by obtaining values that evaluate the functions of the heart based on differences among images obtained of a moving heart during a plurality of phases. In the case that the heart is imaged during a plurality of phases, it is desirable for the functional images to be generated from images obtained during a plurality of phases with an MRI apparatus, which does not expose patients to radiation.

In the description of the present embodiment, a cardiac function image that represents myocardial wall thicknesses which is displayed by the bull's eye display method is generated as a functional image. A morphological image that represents the morphology of blood vessels which are present along the outer myocardial walls of the heart and the like is superimposed on the functional image to generate a bull's eye image. The method by which the bull's eye image is generated will be described later.

The projected three dimensional image generating section 12 generates a projected three dimensional image that represents the three dimensional morphology of a subject, based on the three dimensional medical image data acquired by imaging the subject with a CT apparatus or an MRI apparatus. The projected three dimensional image is an image that represents the three dimensional form of the subject when the subject is viewed from a predetermined projection direction. An initial projection direction of the projected three dimensional image is set in advance. However, the projection direction can changed to a desired projection direction from the initially set projection direction.

When a predetermined position within the functional image which is displayed on the display 3 is specified by a user, the projected three dimensional image generating section 12 of the present embodiment obtains a projection direction that causes a position within the projected three dimensional image corresponding to the specified predetermined position to face forward, and generates a projected three dimensional image projected in this projection direction. That is, the projected three dimensional image generating section 12 of the present embodiment generates a projected three dimensional image, of which the projection direction has been changed from the initially set projection direction to the aforementioned projection direction. Note that the method by which the projected three dimensional image having the changed projection direction is generated will be described later.

The display control section 13 displays the functional image generated by the functional image generating section 11 and the projected three dimensional image generated by the projected three dimensional image generating section 12 on the display 3.

The a specified position data obtaining section 14 obtains data regarding the predetermined position specified within the functional image which is displayed on the display 3 using the input devices 4. The a specified position data obtaining section 14 outputs the obtained specified position data to the projected three dimensional image generating section 12.

The storage device 2 is configured to store three dimensional medical image data 5 acquired by imaging a subject with a CT apparatus, an MRI apparatus, and the like.

The input devices 4 are configured to receive input of predetermined settings from the user. In particular, the input devices 4 of the present embodiment are configured to receive specification of a predetermined position within the functional image which is displayed on the display 3.

Next, the operation of the medical image display system of the present embodiment will be described with reference to the flow chart illustrated in FIG. 2.

First, the functional image generating section 11 of the medical image display apparatus 1 reads out three dimensional medical image data from the storage device 2, and the functional image generating section 11 generates a functional image using the read out three dimensional medical image data (S10). Here, as described above, a cardiac function image that represents myocardial wall thicknesses which is displayed by the bull's eye display method is generated as a functional image. A morphological image that represents the morphology of blood vessels which are present along the outer myocardial walls of the heart and the like is superimposed on the functional image to generate a bull's eye image.

Specifically, the functional image generating section 11 approximates a surface model of the heart with an elliptical shape E such as that illustrated in FIG. 3, based on the three dimensional medical image data representing the heart, to determine a major axis $A_1$ and a minor axis $A_2$ of the heart. The major axis $A_1$ is determined such that it extends from the base of the heart toward the apex of the heart, and passes through the center of a ventricle region. In addition, the minor axis $A_2$ is perpendicular to the major axis $A_1$.

Myocardial wall thicknesses are obtained by generating cross sectional images of slice planes $P_1, P_2, \ldots, P_i, \ldots, P_{N-1}, P_N$ which are the heart cut at constant intervals in a direction that traverses the major axis $A_1$, that is, the direction of the minor axis $A_2$. For example, the contour of the endocardium and the contour of the epicardium are extracted from a slice plane $P_i$ as shown in FIG. 4. The distances between the contour of the endocardium and the contour of the epicardium along lines $l_1, l_2, l_3, \ldots, l_i, \ldots, l_m$ that extend radially from a point C, through which the major axis passes within the ventricle region, are obtained as wall thicknesses d.

Figure 5:
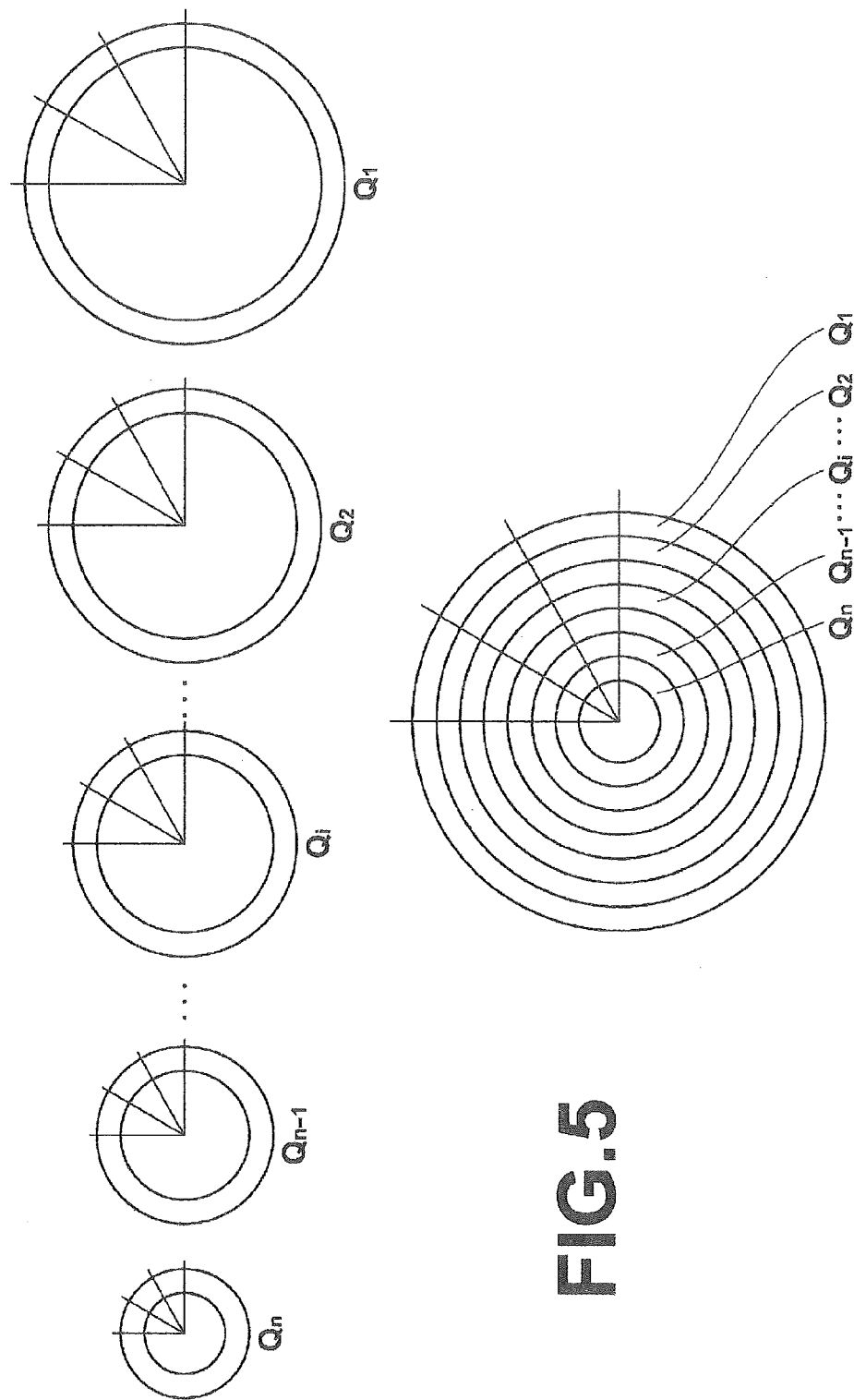
FIG. 5 is a diagram for explaining bull's eye display.

During bull's eye display, display is performed with different colors according to myocardial wall thicknesses d. The wall thicknesses d of slice planes $P_1, P_2, \ldots$ close to the base of the heart are displayed as concentric circles toward the exterior, and the wall thicknesses d of slice planes $P_N$, $P_{N-1}, \ldots$ close to the apex of the heart are displayed as concentric circles toward the interior. In addition, minor axis images, in which the wall thickness d along lines $l_1, l_2, l_3, \ldots, l_i, \ldots, l_m$ of each slice plane Pi is displayed within concentric circles $Q_i$ corresponding to angles formed by the lines $l_1, l_2, l_3, \ldots, l_i, \ldots, l_m$ and a reference line L. As illustrated in FIG. 5, the minor axis images are superimposed on concentric circles $Q_1, Q_2, \ldots, Q_i, \ldots, Q_{n-1}, Q_n$ which are generated in this manner, to generate a functional image in bull's eye display.

Further, the image functional image generating section 11 generates a morphological image representing the morphology of structures such as a blood vessel along the outer wall of the heart myocardium, based on the three dimensional medical image data. Information regarding the coronary artery running along the outer wall myocardium is important in the morphology image. Therefore, a surface model of the heart that includes the coronary arteries is generated. First, coronary arteries that run along the outer myocardial wall is extracted, then a continuous curved surface is estimated by interpolating among the cores and by fitting functions such as a spline function, thereby generating the surface model. Further, the surface model approximates an elliptical shape E such as that illustrated in FIG. 3 in a manner similar to the case in which the aforementioned bull's eye image was generated, to determine the major axis $A_1$ and the minor axis $A_2$ of the heart.

Slice planes Pi that traverse the major axis $A_1$ are generated. The pixel values of blood vessels are large values, and therefore it is possible to project the blood vessels by administering an MIP process on voxel data that include blood vessels. The MIP process is administered using voxel data which are present within a range of a constant distance D along each of a plurality of lines that extend radially from the center C (the point at which the slice plane intersects with the major axis $A_1$) of each slice image $P_i$. The maximum pixel value (hereinafter, referred to as "MIP value") which is obtained by searching within the range of the distance D along each line with the MIP process is projected and displayed as a bull's eye image, to generate the morphology image. By performing the MIP process with the intervals among the slice planes $P_1, P_2, \ldots, P_i, \ldots, P_{N-1}$, $P_N$ to be as small as possible, the state in which blood vessels such as the coronary arteries run along the outer myocardial wall can be observed in greater detail. In addition, the MIP values of The slice planes $P_1, P_2, \ldots$ close to the base of the heart are displayed as concentric circles away from the center and toward the exterior. The MIP values of slice planes $P_N, P_{N-1}, \ldots$ close to the apex of the heart are displayed as concentric circles close to the center and toward the interior.

The functional image generating section 11 generates a bull's eye image in which the functional image and the morphology image generated as described are superimposed, and outputs the bull's eye image to the display control section 13.

Meanwhile, the projected three dimensional image generating section 12 of the medical image display apparatus 1 reads out three dimensional medical image data from the storage device 2, and the projected three dimensional image generating section 12 generates a projected three dimensional image using the read out three dimensional medical image data (S10). Note that the projected three dimensional image which is generated at this time is a projected three dimensional image which is projected in the aforementioned initially set projection direction. Note that methods for generating projected three dimensional images are known, and therefore a description thereof will be omitted.

In addition, the projected three dimensional image generating section 12 of the present embodiment generates an image in which the colors of the functional image are superimposed on the aforementioned projected three dimensional image. The method disclosed in Japanese Unexamined Patent Publication No. 2001-181041 may be applied as the method for superimposing the colors of the bull's eye image onto the projected three dimensional image, for example. Hereinafter, the image in which the colors of the functional image are superimposed on the projected three dimensional image will be referred to simply as a "projected three dimensional image".

The projected three dimensional image generating section 12 outputs the three dimensional projection image generated in the manner described above to the display control section 13.

Figure 6:
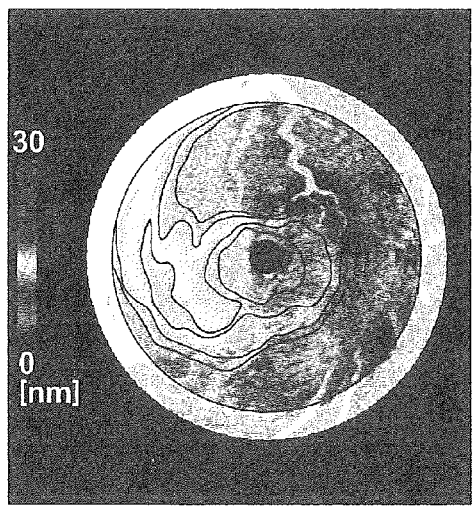
FIG. 6 is a diagram that illustrates an example of a bull's eye image.
Figure 7:
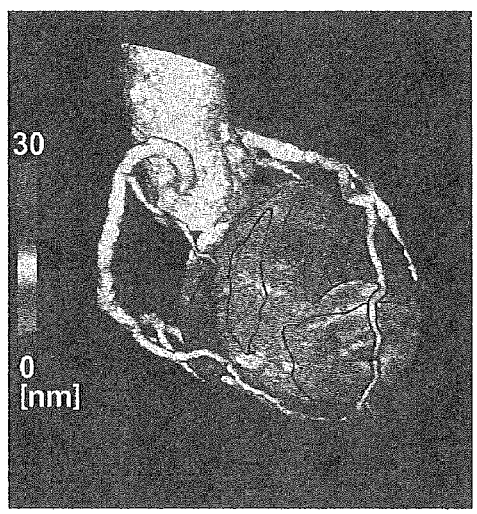
FIG. 7 is a diagram that illustrates an example of a projected three dimensional image.

The display control section 13 displays the input bull's eye image and projected three dimensional image side by side on the display 3 (S12). FIG. 6 is a diagram that illustrates an example of a bull's eye image. FIG. 7 is a diagram that illustrates an example of a projected three dimensional image.

Figure 8:
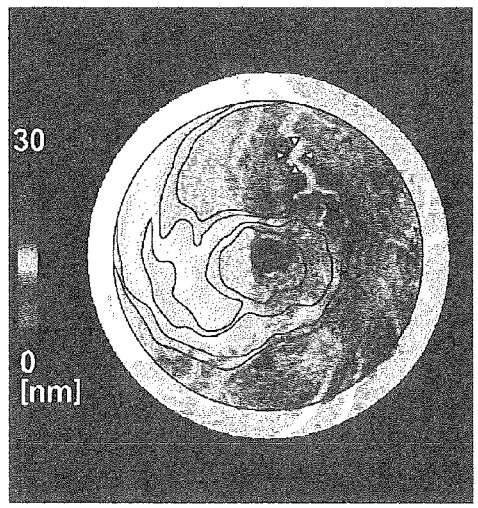
FIG. 8 is a diagram for explaining a case in which a predetermined position is specified within a bull's eye image.

Next, a position or a region which is desired to be observed is specified within the bull's eye image by a user (S14). The position is specified by use of the input devices 4, for example, and performed by specifying a position with a cursor or the like which is displayed on the display 3. FIG. 8 illustrates an example in which a mark is displayed at a position specified within a bull's eye image.

When the predetermined position is specified within the bull's eye image by the user, position data of the specified position is obtained by the specified position data obtaining section 14 (S16). The position data obtained by the specified position data obtaining section 14 is output to the projected three dimensional image generating section 12.

When the predetermined position is specified by the user within the bull's eye image, the projected three dimensional image generating section 12 obtains a projection direction that will cause a position within the projected three dimensional image that corresponds to the specified predetermined position to face forward, and generates a projected three dimensional image which his projected in the obtained projection direction (S18). That is, the projected three dimensional image generating section 12 generates a projected three dimensional image, of which the projection direction has been changed from the initially set projection direction to the aforementioned projection direction. Note that in the present embodiment, the position within the projected three dimensional image that corresponds to the specified predetermined position is a position within the projected three dimensional image at the same position on the heart as the specified predetermined position.

Figure 9:
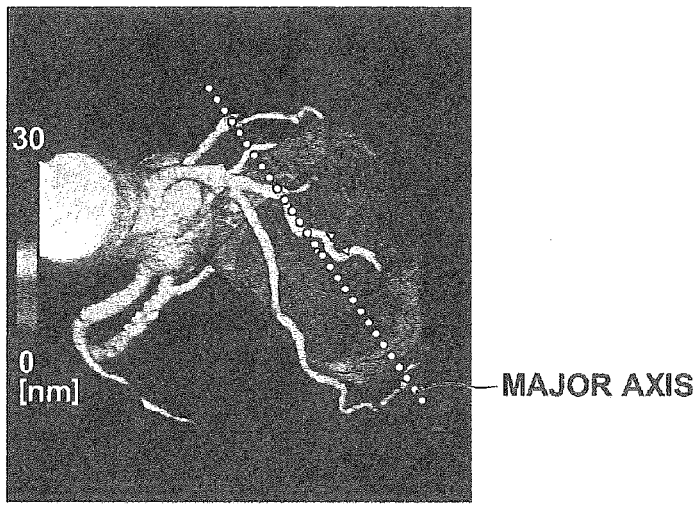
FIG. 9 is a diagram that illustrates an example in which a projected three dimensional image is generated by rotating a heart with the major axis thereof as an axis of rotation and projected in a new projection.

Specifically, the projected three dimensional image generating section 12 of the present embodiment sets the major axis of the heart as an axis of rotation as illustrated in FIG. 9, obtains a new projection direction which is rotated for a predetermined amount of rotation from the initially set projection direction, and generates a projected three dimensional image which is projected in the new projection direction. Note that the major axis of the heart is the same as the major axis which was set when generating the functional image. FIG. 9 illustrates a projected three dimensional image having the new projection direction.

Here, the method for obtaining the aforementioned new projection direction will be described.

Figure 10:
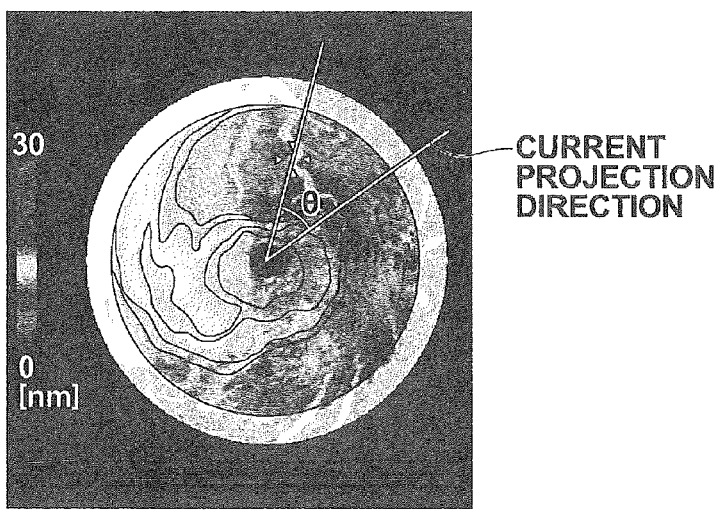
FIG. 10 is a diagram for explaining a method for determining an amount of rotation from a current projection direction.

First, as illustrated in FIG. 10, a straight line that connects the center of the bull's eye image and the specified position (the marked position shown in FIG. 9) within the bull's eye image is determined. Then, an angle θ formed between this line and the current projection direction (here, the initially set projection direction) is obtained.

At this time, when the direction of the major axis of the heart is designated as unit vector v, a rotation matrix $M_θ$ that represents the amount of rotation to be obtained can be expressed by Formula (1) below.

[Formula 1]

$$M_\theta = \begin{bmatrix} (1-\cos\theta)\vec{v}_x^2 + \cos\theta & (1-\cos\theta)\vec{v}_x\vec{v}_y + \vec{v}_z\sin\theta & (1-\cos\theta)\vec{v}_x\vec{v}_z - \vec{v}_y\sin\theta \\ (1-\cos\theta)\vec{v}_x\vec{v}_y - \vec{v}_z\sin\theta & (1-\cos\theta)\vec{v}_y^2 + \cos\theta & (1-\cos\theta)\vec{v}_y\vec{v}_z + \vec{v}_x\sin\theta \\ (1-\cos\theta)\vec{v}_x\vec{v}_z + \vec{v}_y\sin\theta & (1-\cos\theta)\vec{v}_y\vec{v}_z - \vec{v}_x\sin\theta & (1-\cos\theta)\vec{v}_z^2 + \cos\theta \end{bmatrix}$$

Then, a new projection direction M can be obtained by multiplying the current projection direction $M_n$ and the rotation matrix $N_θ$ as shown in Formula (2) below.

$$M = M_n M_\theta \qquad \text{[Formula 2]}$$

Figure 11:
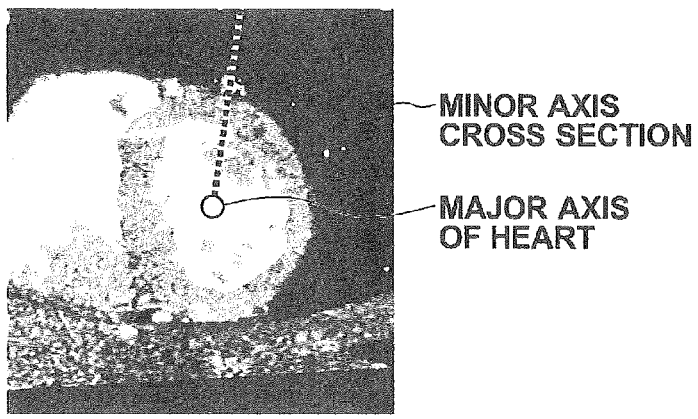
FIG. 11 is a diagram for explaining a method for determining the point of view of a projected three dimensional image in a new projection direction.

Meanwhile, with respect to the viewpoint position (camera position) of the projected three dimensional image, a line segment that connects the major axis of the heart and the specified position (the marked position shown in FIG. 11) is set within a minor axis cross section corresponding to the position specified within the bull's eye image that perpendicularly intersects the major axis of the heart, as shown in FIG. 11. The viewpoint position is set at a point along an extended line (the dotted line shown in FIG. 11) which is the line segment extended toward the specified position. Generally, projected three dimensional images for use as medical images undergo parallel projection. Therefore, the same projection results can be obtained as long as the viewpoint position is not place within the interior of the heart.

By generating the new projected three dimensional image based on the new projection direction and viewpoint position, the projected three dimensional image generating section 12 generates a projected three dimensional image in which the position which is specified within the bull's eye image faces forward.

Also, at this time, the projected three dimensional image generating section 12 determines the position within the projected three dimensional image which is the same position of the heart as the location specified within the bull's eye image, and places a marker at this position. Specifically, the distance between the marked position in the bull's eye image illustrated in FIG. 9 and the center of bull's eye image is obtained. The marked position within the projected three dimensional image prior to rotation is obtained, based on this distance and the position of the marked position within the bull's eye image in the circumferential direction. Then, the marked position is rotated for the amount of rotation θ with the major axis of the heart as the axis of rotation, to obtain the marked position within the new projected three dimensional image.

Next, the new projected three dimensional image, generated by the projected three dimensional image generating section 12 is output to the display control section 13, and the display control section 13 displays the new projected three dimensional image having the marker as shown in FIG. 9 therein on the display 3 (S20). Note that the major axis of the heart shown in FIG. 9 is not displayed on the display.

According to the medical image display system of the first embodiment, both a functional image and a projected three dimensional image are displayed on the display 3. When a predetermined position is specified within the functional image which is displayed on the display section, a projected three dimensional image which is projected in a projection direction such that the position within the projected three dimensional image corresponding to the specified predetermined position faces forward, based on data regarding the specified predetermined position. The generated projected three dimensional image projected in the projection direction is displayed. Therefore, the morphology of blood vessels or the like which are at the position within the projected three dimensional image corresponding to the position within the functional image can be easily and expediently observed.

Figure 12:
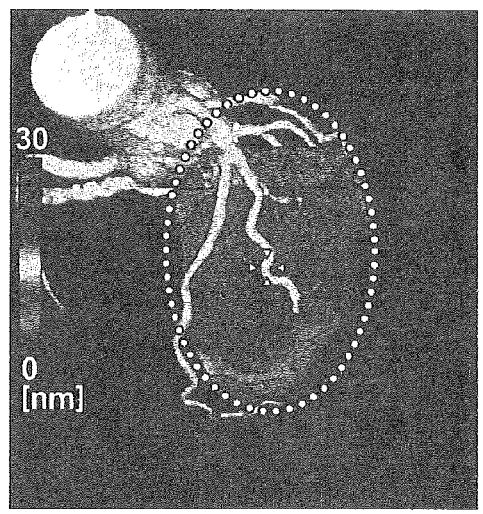
FIG. 12 is a diagram that illustrates an example of a projected three dimensional image which is projected in a projection direction such that a line segment that connects the center of an ellipsoidal shape that approximates the heart and the position within the projected three dimensional image is directed forward.

Note that in the description of the first embodiment, the projected three dimensional image generating section 12 rotates the projected three dimensional image using the major axis of the heart as the axis of rotation. However, the present invention is not limited to such a configuration. For example, a configuration may be adopted, wherein a rotation process is administered such that a line segment that connects the center of an ellipsoidal shape that approximates the heart as illustrated in FIG. 12 and the position within the projected three dimensional image that corresponds to the position specified within the bull's eye image is directed forward, and a new projected three dimensional image which is projected in the new projection direction is generated. FIG. 12 illustrates a projected three dimensional image which is projected in a new projection direction, generated in the manner described above.

Figure 13:
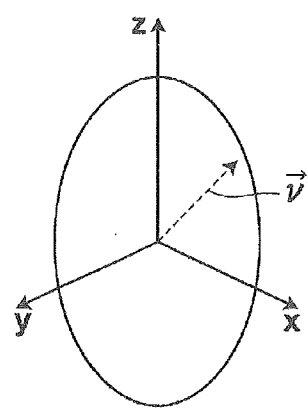
FIG. 13 is a diagram for explaining a method for generating the projected three dimensional image illustrated in FIG. 12.

Specifically, for example, it is possible to determine the position within the projected three dimensional image at the same the position of the heart as the location specified within the bull's eye image as described above. Therefore, the direction that passes through this position and the center of the ellipse is designated as a unit vector v. In addition, if the direction of the major axis of the heart (ellipse) is designated as z as shown in FIG. 13, the direction of the line of sight is designated as the unit vector v, and a rotation matrix M that causes the direction of the line of sight to become a vector z can be obtained by Formula (3) below.

$$\vec{v}_1 = \vec{z} \times \vec{v}$$

$$\vec{v}_2 = \vec{v}_1 \times \vec{v}$$

$$M = (\vec{v}_1\ \vec{v}_2\ \vec{v}) \qquad \text{[Formula 3]}$$

In addition, in the description of the first embodiment, a change from display of a projected three dimensional image projected in the initially set projection direction to display of a projected three dimensional image projected in the new projection direction was described. In the case that a different position is further specified within the bull's eye image, a new projection direction that causes a position within the projected three dimensional image that corresponds to the different specified position to face forward is obtained. A projected three dimensional image which is projected in the newly obtained projection image is generated, and display can be changed from the projected three dimensional image projected in the current projection direction to display of a projected three dimensional image projected in the new projection direction. That is, new projection directions that cause positions within the projected three dimensional image that correspond to positions specified within the bull's eye image to face forward may be sequentially obtained, and projected three dimensional images may be sequentially generated and displayed such that the positions within the projected three dimensional images that correspond to positions specified within the bull's eye image are constantly facing forward.

In addition, in the description of the first embodiment, the display is switched from display of a projected three dimensional image projected in a current projection direction to display of a projected three dimensional image projected in the new projection direction in a two step process. However, the present invention is not limited to such a configuration. A configuration may be adopted, wherein a plurality of projection directions are obtained between the current projection direction and the new projection direction at predetermined intervals, a plurality of projected three dimensional images are generated for each of the plurality of projection directions and sequentially displayed, such that the change from display of the projected three dimensional image projected in the current projection direction to display of the projected three dimensional image projected in the new projection direction becomes continuous.

Next, a medical image display system equipped with a second embodiment of the present invention will be described. The schematic configuration of the medical image display system of the second embodiment is the same as that of the medical image display system of the first embodiment, illustrated in FIG. 1.

In the medical image display system of the first embodiment described above, new projection directions are obtained and projected three dimensional images are generated such that the position specified within a bull's eye image constantly faces forward. However, in this case, new projection directions are sequentially obtained each time that the position specified within the bull's eye image is changed, and display of the projected three dimensional image also changes sequentially according to the newly obtained projection directions.

However, in the case that positions are specified within the bull's eye image by specifying the position of a cursor displayed on the display 3 with a mouse or the like, there are cases in which the position of the cursor fluctuates due to the movement of the user's hand. If the display of the projected three dimensional image is changed according to the position of the cursor in such cases, the projection direction of the projected three dimensional image will be finely changed against the user's intentions, and the display may become that which is extremely difficult for the user to observe.

Therefore, in the medical image display system of the second embodiment, fine changes in the projection direction of the projected three dimensional image are prevented even if the position of a cursor fluctuates as described above, while a range of the projected three dimensional image which is desired to be observed is constantly displayed facing forward.

Figure 14:
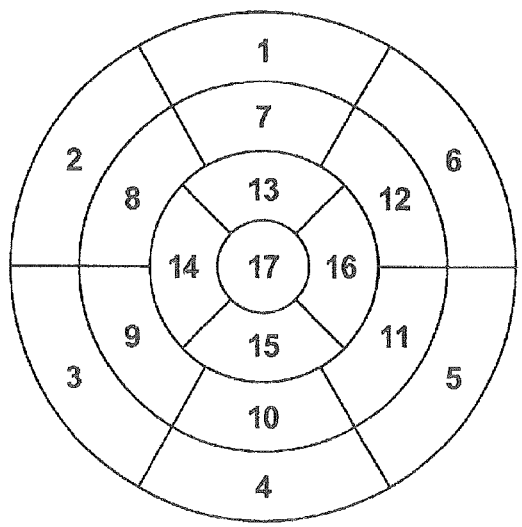
FIG. 14 is a diagram in which a functional image is sectioned into 17 regions.

Specifically, as shown in FIG. 14, a projected three dimensional image generating section 12 of the present embodiment divides the interior of bull's eye images into 17 regions. The projected three dimensional image generating 12 identifies a sectioned region from among the 17 sectioned regions that includes the position specified within the bull's eye image by a user, that is, position data obtained by a specified position data obtaining section 14. Then, the projected three dimensional image generating 12 generates a projected three dimensional image projected in a projection direction such that a position, which is set in advance, within the identified sectioned region faces forward.

Here, the sectioned regions are regions which divide the bull's eye image into a plurality of concentric sections, which are further divided into a plurality of sections in the circumferential direction, as illustrated in FIG. 14. These are regions which are set based on a myocardial segment model in nuclear cardiology. Specifically, the sectioned regions are set based on a 17 segment model, which is constituted by minor axis images of the myocardia at the base of the heart and at the central portion of the heart, each of which is divided into 6 segments, a minor axis image at the apex of the heart divided into 4 segments, and one segment at the apex of the heart, for a total of 17 segments. However, the segmented regions need not necessarily be based on the 17 segment model, and may alternatively be set based on other segment models, such as a 4 segment model, a 9 segment model, and a 20 segment model.

As described above, the projected three dimensional image generating section 12 identifies a sectioned region from among the 17 sectioned regions that includes the position specified within the bull's eye image by a user, and obtains a position, which is set in advance within the sectioned region. In the present embodiment, the position which is set in advance is the center position of the identified sectioned region.

Figure 15:
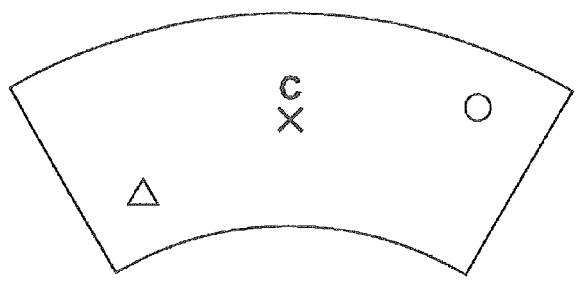
FIG. 15 is a diagram for explaining the center position of a sectioned region.
Figure 16:
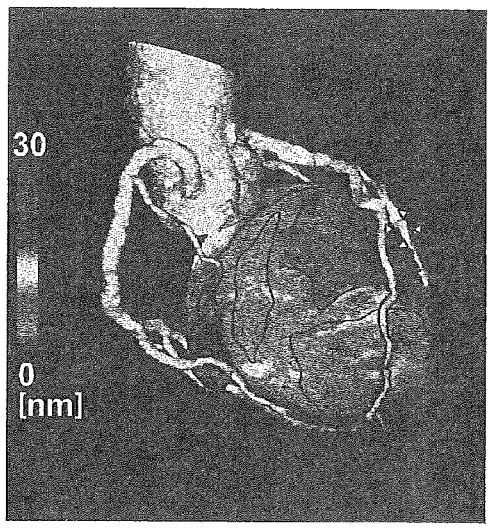
FIG. 16 is a diagram that illustrates an example of a display of a position within a functional image within a projected three dimensional image by a conventional method.
Figure 17:
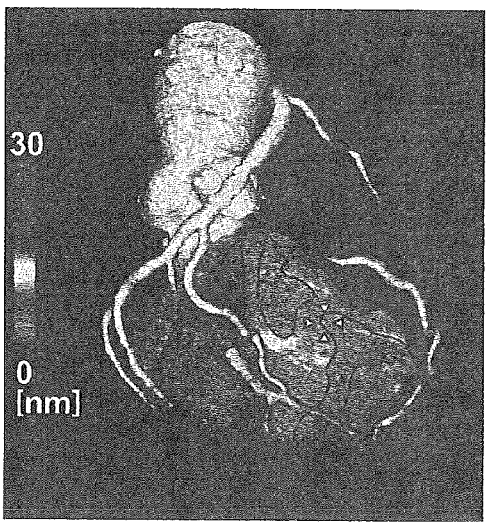
FIG. 17 is a diagram that illustrates an example of a display of a position within a functional image within a projected three dimensional image by a conventional method.

Specifically, if the position specified by the user within the bull's eye image is included within sectioned region "7" from among the 17 sectioned regions illustrated in FIG. 14, that is, if the position indicated by the circle or the triangle in FIG. 15 is specified, the center position C of the sectioned region "7" is obtained. Note that the central position C is the central position within the sectioned region "7" in both the radial direction and the circumferential direction. In the case that the position specified by the user is included in a sectioned region other than sectioned region "7", the center position C in the radial direction and the circumferential direction within the sectioned region may be obtained. In the case that the position specified by the user is included in sectioned region "17", the center position C of the circle is obtained.

The projected three dimensional image generating section 12 of the present embodiment generates a projected three dimensional image which is projected in a projection direction such that the center position C of the sectioned region obtained in the manner described above faces forward. That is, even if different positions (for example, the position of the circle and the position of the circle illustrated in FIG. 15) are specified in the bull's eye image, as long as the positions are included in the same sectioned region, a three dimensional image which is projected in the same projection direction is generated. Accordingly, even if the position specified by the user is slightly modified by the movement of the user's, if the position is within the same sectioned region, the display of the projected three dimensional image in the same projection direction is maintained. Note that in the present embodiment, the center position C of the sectioned region is the position that faces forward. However, the position that faces forward need not necessarily be the center position of the sectioned region, and other positions may be set within the sectioned regions in advance.

In the case that the position specified by the user moves into a different sectioned region, a projected three dimensional image, which is projected in a projection direction such that the center position C of the different sectioned region faces forward, is generated and displayed.

By changing the projection direction of the projected three dimensional image in the manner described above, the projection direction of the projected three dimensional image being finely changed can be prevented, while a region which is desired to be observed, that is, a sectioned region which is set by the segment model of the myocardia, can be displayed constantly facing forward.

Note that with respect to a method for generating the projected three dimensional image which is projected in a projection direction such that the center position C within the segmented region faces forward, a new projection direction was obtained employing the position specified by the user in the first embodiment, whereas in the second embodiment, the center position C within the segmented region is employed instead of the position specified by the user. Therefore, a detailed description will be omitted.

Note that in the second embodiment as well, display may be switched from a projected three dimensional image which is projected in a current projection direction to a projected three dimensional image which is projected in a new projection direction in a continuous manner, as in the first embodiment.

What is claimed is:
1. A medical image display control apparatus, comprising:
    a functional image generating section that generates a functional image that represents functions of a subject, based on three dimensional medical image data obtained by imaging the subject;

a projected three dimensional image generating section that generates a projected three dimensional image that represents a three dimensional appearance of the subject, based on three dimensional medical image data obtained by imaging the subject;

a display control section that displays the functional image and the projected three dimensional image on a display section; and a specified position data obtaining section that obtains data regarding a predetermined position which is specified within the functional image which is being displayed on the display section wherein the projected three dimensional image generating section automatically generates the projected three dimensional image which is projected in a projection direction such that a position within the projected three dimensional image corresponding to the specified predetermined position faces forward, based on the data regarding the predetermined specified position, when the predetermined position is specified within the functional image by an operation that specifies the predetermined position, and wherein the display control section displays the projected three dimensional image having the projection direction on the display section.

2. A medical image display control apparatus as defined in claim 1, wherein the position within the projected three dimensional image is the same as a position on the subject represented by the data regarding the position obtained by the specified position data obtaining section.

3. A medical image display control apparatus as defined in claim 1, wherein the position within the projected three dimensional image comprises a position which is set in advance within a sectioned region of the functional image that includes the position data obtained by the specified position data obtaining section from among a plurality of sectioned regions into which the functional image is divided.

4. A medical image display control apparatus as defined in claim 3, wherein the position which is set in advance within the sectioned region is the center position of the sectioned region.

5. A medical image display control apparatus as defined in claim 3, wherein the sectioned regions are regions which are divided into a plurality of concentric regions and then further divided into a plurality of regions in the circumferential direction.

6. A medical image display control apparatus as defined in claim 3, wherein the sectioned regions are those in which the functional image is divided into seventeen regions.

7. A medical image display control apparatus as defined in claim 1, wherein:
the subject comprises a heart; and
the projected three dimensional image generating section generates the projected three dimensional image in the projection direction by administering a rotation process with the longitudinal direction of the heart as an axis of rotation.

8. A medical image display control apparatus as defined in claim 1, wherein:
the subject comprises a heart; and
the projected three dimensional image generating section generates the projected three dimensional image in the projection direction by administering a rotation process such that a line segment that connects the center of an ellipsoidal shape that approximates the heart and the position within the projected three dimensional image is directed forward.

9. A medical image display control apparatus as defined in claim 1, wherein the projected three dimensional image is newly generated such that a selected region faces forward and is displayed.

10. A medical image display control apparatus as defined in claim 1, wherein, in a case that the projected three dimensional image is displayed at a position which has a predetermined difficulty to view, the projected three dimensional image generating section automatically generates and the display control section displays the projected three dimensional image facing forward without additional operations being input by a user.

11. A medical image display control apparatus as defined in claim 1, wherein the projected three dimensional image comprises an image that represents the three dimensional shape of the subject when the subject is viewed from a predetermined projection direction.

12. A medical image display control apparatus as defined in claim 1, wherein the functional image comprises an image representing a distribution of evaluation values that represent evaluations of functions of the heart.

13. A medical image display control apparatus as defined in claim 1, wherein the projected three dimensional image generating section sets a major axis of the subject as an axis of rotation, obtains the projection direction which is rotated for a predetermined amount of rotation from an initially set projection direction, and generates the projected three dimensional image which is projected in the projection direction.

14. A medical image display control method, comprising:
generating a functional image that represents the functions of a subject, based on three dimensional medical image data obtained by imaging the subject;
generating a projected three dimensional image that represents a three dimensional appearance of the subject, based on three dimensional medical image data obtained by imaging the subject; and
displaying the functional image and the projected three dimensional image on a display section;
data being obtained regarding a predetermined position which is specified within the functional image which is being displayed on the display section when the predetermined position is specified within the functional image
wherein the projected three dimensional image which is projected in a projection direction such that a position within the projected three dimensional image corresponding to the specified predetermined position faces forward is automatically generated, based on the data regarding the predetermined specified position when the predetermined position is specified within the functional image by an operation that specifies the predetermined position, and
wherein the projected three dimensional image having the projection direction is displayed on the display section.

15. A non-transitory computer readable medium having a medical image display control program recorded therein, the program causing a computer to function as:
a functional image generating section that generates a functional image that represents the functions of a subject, based on three dimensional medical image data obtained by imaging the subject;
a projected three dimensional image generating section that generates a projected three dimensional image that represents a three dimensional appearance of the subject, based on three dimensional medical image data obtained by imaging the subject;

a display control section that displays the functional image and the projected three dimensional image on a display section; and a specified position data obtaining section that obtains data regarding a predetermined position which is specified within the functional image which is being displayed on the display section, wherein the projected three dimensional image generating section automatically generates the projected three dimensional image which is projected in a projection direction such that a position within the projected three dimensional image corresponding to the specified predetermined position faces forward, based on the data regarding the predetermined specified position, when the predetermined position is specified within the functional image by an operation that specifies the predetermined position, and wherein the display control section displays the projected three dimensional image having the projection direction on the display section.

* * * * *